(12) United States Patent
Watling

(10) Patent No.: US 6,840,744 B2
(45) Date of Patent: Jan. 11, 2005

(54) CONTINUOUS LIQUID FLOW SYSTEM

(75) Inventor: David Watling, Wescott (GB)

(73) Assignee: Bioquell UK Limited, Andover Hampshire (GB)

(*) Notice: Subject to any disclaimer, the term of this patent is extended or adjusted under 35 U.S.C. 154(b) by 100 days.

(21) Appl. No.: 10/203,992

(22) PCT Filed: Mar. 15, 2001

(86) PCT No.: PCT/GB01/01145

§ 371 (c)(1),
(2), (4) Date: Aug. 15, 2002

(87) PCT Pub. No.: WO01/71297

PCT Pub. Date: Sep. 27, 2001

(65) Prior Publication Data

US 2003/0071053 A1 Apr. 17, 2003

(30) Foreign Application Priority Data

Mar. 21, 2000 (GB) .............................................. 0006825

(51) Int. Cl.⁷ .......................... F04B 25/00; F04B 49/00; B67D 5/08; B67D 5/16
(52) U.S. Cl. ........................... 417/249; 417/43; 417/37; 222/56; 222/71
(58) Field of Search ...................... 222/56, 71; 417/36, 417/37, 38, 43, 211.5, 249, 474

(56) References Cited

U.S. PATENT DOCUMENTS

| | | | |
|---|---|---|---|
| 3,128,782 A | * | 4/1964 | Limpert et al. ................. 137/1 |
| 3,252,618 A | * | 5/1966 | Anderson et al. ............... 222/1 |
| 3,836,285 A | * | 9/1974 | Purtell .......................... 417/34 |
| 5,316,444 A | | 5/1994 | Wicnienski |
| 5,402,670 A | * | 4/1995 | Wicnienski .................. 73/32 A |

FOREIGN PATENT DOCUMENTS

| | | | | |
|---|---|---|---|---|
| EP | 0 662 844 B1 | | 3/1998 | |
| GB | 2 354 443 A | | 3/2001 | |
| JP | 10-104046 | * | 4/1998 | .......... G01G/11/00 |
| WO | WO 94/07544 A1 | | 4/1994 | |

* cited by examiner

*Primary Examiner*—Justine R. Yu
*Assistant Examiner*—Timothy P. Solak
(74) *Attorney, Agent, or Firm*—Workman Nydegger

(57) ABSTRACT

A system for continuous delivery of a measured flow of liquid to a processing apparatus includes a reservoir for holding a bulk supply of the liquid and an intermediate vessel. A first pump delivers liquid from the intermediate vessel to processing equipment at one rate. A second pump delivers liquid from the reservoir to the intermediate vessel at a second much faster rate. A monitor device continuously monitors the weight of the vessel and controls the first pump accordingly to deliver the required weight of liquid at the required rate to the processing equipment. The monitoring device determines when the weight of liquid in the intermediate vessel has reached a minimum position to initiate operation of the second pump to refill to vessel and a further device terminates operation of the second pump when the liquid level in the vessel reaches a maximum position.

8 Claims, 1 Drawing Sheet

CONTINUOUS LIQUID FLOW SYSTEM

BACKGROUND OF THE INVENTION

1. Field of the Invention

The present invention relates to a method of continuously measuring the flow of a liquid. Pumping liquids often results in the generation of bubbles which make it difficult to measure and control with conventional flow measuring devices.

2. The Relevant Technology

In the field of gaseous phase sterilisation the most common method to generate the vapour is by evaporating an aqueous solution of the sterilant on a hot surface. Typically, the solution would be 35% w/w hydrogen peroxide. Such solutions tend to be unstable and give off bubbles of gas, which interfere with the conventional flow measuring systems.

This problem was recognised and dealt with in EP O 662 844 B1, by drawing the sterilising solution from a container into an accumulator and measuring the weight loss in the container. Whilst this technique allows for a known weight of liquid to be delivered to the evaporator and then to turn this weight of liquid into a vapour it has two shortcomings. Firstly, it is necessary to decide at the start of the process how much liquid will be required, and secondly it limits the amount of liquid that may be dispensed. The apparatus described in EPO 662 844 B1 requires that the liquid flow rate to the evaporator is greater than the flow rate used to fill the accumulator. This difference in the flow rate means that the accumulator cannot be refilled from the container as the flow from the accumulator will always be greater than the flow with the accumulator.

It is also important in gaseous sterilisation process to be able to control the concentration of the gas being delivered to the chamber to be sterilised. The concentration will depend on the mass flow of the carrier gas, normally air, and the rate at which liquid is evaporated into the air stream. The present invention not only deals with the first two difficulties found in Patent EPO 662 844 B1 but also provides a method of measuring and controlling the liquid flow to the evaporator.

SUMMARY OF THE INVENTION

An object of the present invention is to provide a method for continuously delivering a measured flow of liquid to a processing apparatus such as an evaporator when the liquid may be unstable and bubbles may be generated spontaneously in the liquid flow path.

The invention provides a system for continuous delivery of a measured flow of liquid to a processing apparatus comprising a reservoir for holding a bulk supply of the liquid, an intermediate vessel, first means to pump liquid from the intermediate vessel to processing equipment at one rate, second means to pump liquid from the reservoir to the intermediate vessel of a second much faster rate, means to monitor continuously the weight of the vessel and to determine the mass flow rate of liquid form the intermediate vessel and to control the first pump means accordingly to deliver the required weight of liquid at the required rate to the processing equipment, means to determine when the weight of liquid in the intermediate level has reached a minimum position to initiate operation of the second pump means to refill the vessel and means to terminate operation of the second pump means when the liquid level in the vessel reaches a maximum position.

In one specific embodiment according to the invention, the system consists of a primary liquid reservoir, a measuring tube, and pumps to transfer the liquid from the reservoir to the measuring tube, and from the measuring tube to the liquid evaporator. A further pump may be provided to remove any residual liquid from the measuring tube to the reservoir at the end of the sterilisation cycle. It is essential that the delivery rate of the pump feeding the liquid from the reservoir to the measuring tube should be about 20 times faster than the maximum speed of the pump delivering the liquid from the measuring tube to the evaporator. The liquid flow rate required to be delivered from the measuring tube to the evaporator will depend on the mass flow of the carrier gas and the required concentration of the sterilising gas.

The liquid is first pumped from the reservoir into the measuring tube. The pressure at the bottom of the measuring tube will increase with the height of the column of liquid and is measured using a pressure transducer.

When sufficient liquid has been delivered to the measuring tube the pump delivering the liquid will be stopped and the system is ready to start delivering liquid to the evaporator.

As soon as it is required to start the sterilisation process liquid is pumped from the measuring tube to the evaporator, and the rate of change in the height of the column is measured using the pressure transducer. The change of pressure may be converted into a mass flow rate from knowledge of the diameter of the measuring tube. Once this rate of flow is known it may be used to adjust the pump speed to correct any deviations from the selected mass flow. Because this is a genuine mass flow technique it eliminates the effects of bubble formation.

When the level of the liquid in the measuring tube falls to a pre-set low level the filling pump is started and the measuring tube is refilled as before. During the refilling process the delivery pump to the evaporator runs at the last adjusted speed and the mass flow of the liquid in the evaporator is assumed to remain constant.

At the end of the sterilisation process the control system calculates the total mass of liquid delivered to the evaporator from the mass of the liquid delivered from the measuring tube, plus the calculated mass flow during the time taken to re-fill the measuring tube.

BRIEF DESCRIPTION OF THE DRAWINGS

The following is a description of some specific embodiments of the invention, reference being made to the accompanying drawings, in which.

DETAILED DESCRIPTION OF THE PREFERRED EMBODIMENTS

Figure 1:
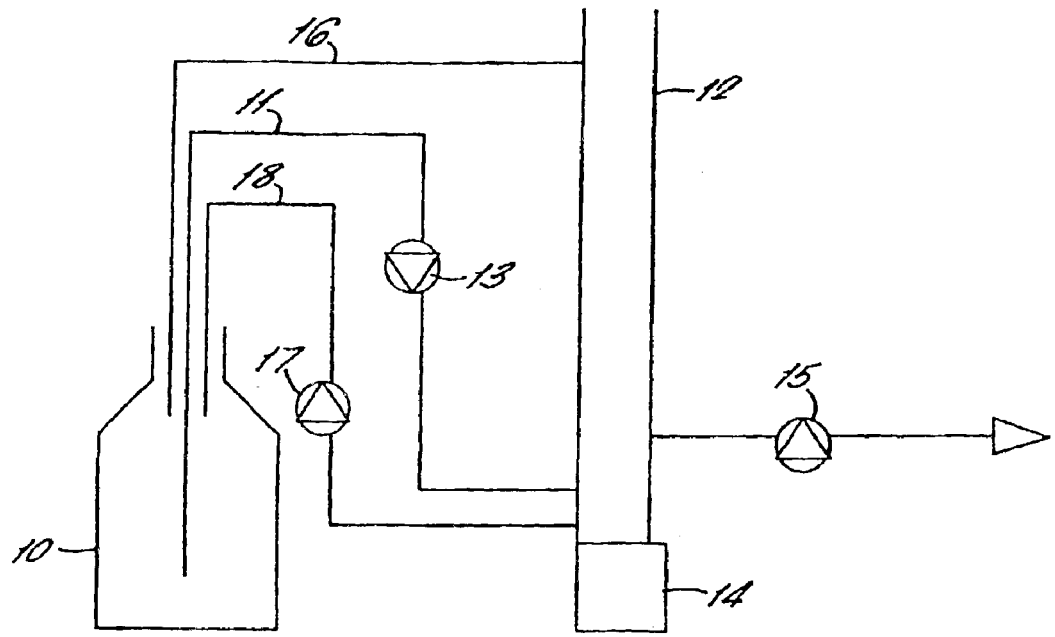
FIG. 1 is a diagrammatic view of a liquid delivery system according to the invention.

Referring firstly to FIG. 1 of the drawings, there is shown an apparatus for producing a measured continuous flow of liquid such as water to a processing apparatus such as an evaporator.

The apparatus consists of a container 10 fluidly connected by a pipe 11 to a column form measuring tube 12 via a pump 13. At the base of the measuring tube is fitted a pressure transducer 14 to measure the pressure exerted by the column of liquid in the measuring tube. A Pump 15 delivers liquid to an evaporator (not shown) from the measuring tube. An overflow tube 16 is provided to connect the top of the measuring tube to the container to return excess fluid to the container should a fault arise and the measuring tube become overfilled. A pump 17 is used to pump excess liquid at the end of the sterilisation process via pipe 18, which fluidly connects the base of the measuring tube to the container.

A control system, typically based on a Programmable Logic Controller (PLC), is used to control the operation of the apparatus. The pump 15 is a variable speed pump typically a peristaltic pump, and may be used to vary the liquid flow rate from the measuring tube to the evaporator. The pump 13 is a fixed speed pump, typically having a mass flow rate about 20 times greater than the maximum delivery rate of pump 15. Pump 17 is used to empty the measuring tube at the end of the cycle and may have any convenient rate. Typically pump 13 and pump 17 are peristaltic pumps, but any other type that is compatible with the liquid would be suitable. The liquid to be evaporated as the sterilizing agent is first pumped from the container through the pipe fluidly connecting the container to the measuring tube by the pump 13, until the required mass of liquid as measured by the Pressure Transducer has been transferred.

Once the measuring tube is full then the system is ready to start delivering the liquid to the evaporator using the pump 15. The initial speed of the pump 15 is set by the control system to give the desired mass flow rate. The initial speed of the pump is set by reference to the data stored in the PLC from the calibration of the pump speed and the flow rate.

Once liquid is delivered to the evaporator by pump 13, the liquid level in the measuring tube will start to fall, and hence the static pressure measured by the pressure transducer will also fall. By monitoring the rate of fall of pressure the PLC is able to calculate the actual delivery rate achieved by pump 15. The PLC is then able to adjust the speed of pump 15 to adjust for any deviation of the actual mass flow from the required mass flow.

Should the sterilisation not be completed when the liquid in the measuring tube falls to the minimum level, then the pump 13 will be started by the PLC filling the measuring tube. During the period of time that it takes for the pump 13 to fill the measuring tube the pump 15 remains running at the last adjusted speed. As soon as the measuring tube is re-filled then automatic adjustment of the speed of pump 15 is resumed to maintain the required mass flow rate.

The number of times that the measuring tube may be re-filled is only limited to the amount of liquid available in the container. Should very long sterilisation processes be required it is possible to replenish the liquid in the container either manually or with a separate automatic system, which senses the level of liquid in container using a dip tube.

At the end of the sterilisation period the pump 17 returns any remaining liquid from the measuring tube to the container. The overflow pipe which fluidly connects the top of the measuring tube to the container is provided in the event of an equipment failure and pump 13 should continue to operate after the measuring tube has been filled.

Further safety features may be programmed into the PLC to ensure that the tube is filled within a fixed period of time, to avoid the problem of a failure of pump 13 or having an empty container.

The total mass flow may be calculated from the change in pressure in the measuring tube, and if necessary adjusted for the liquid delivered while the measuring tube is being re-filled. This adjustment may be made from knowledge of the time taken to re-fill the tube and the flow rate immediately before the re-filling was started.

The measuring tube may be re-filled any number of times and each time this occurs an adjustment must be added to the total mass flow.

The system is particularly suitable for use in the sterilizing apparatus described and illustrated in UK Patent Application No. 9922364.6.

Figure 2:
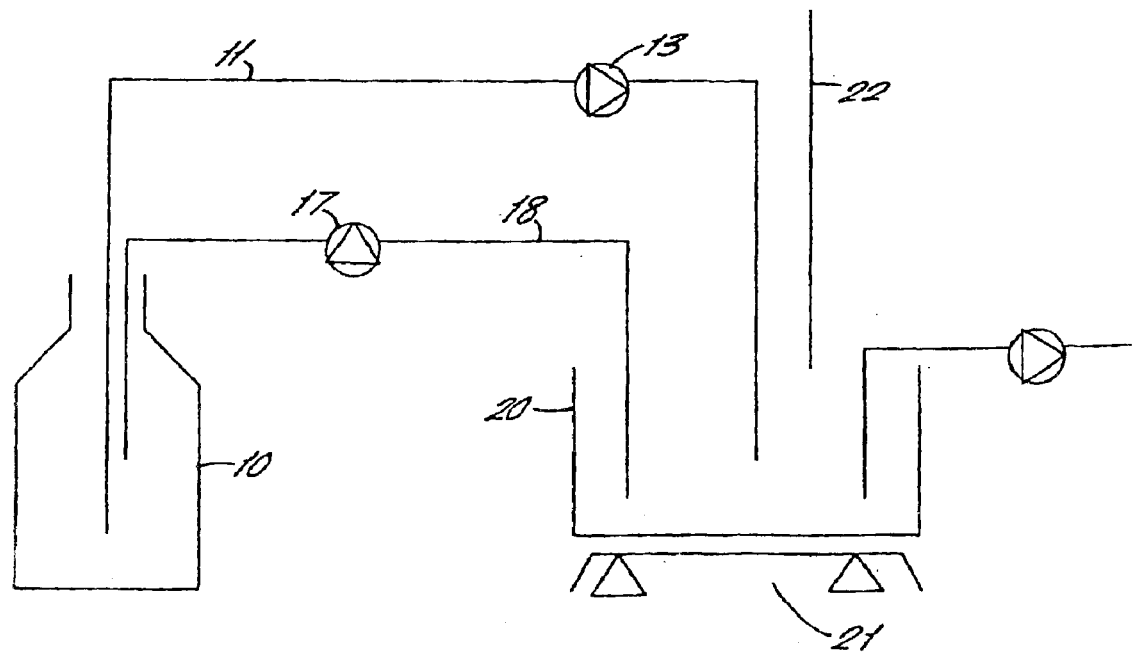
FIG. 2 is a diagram showing a modified arrangement.

An alternative arrangement is shown in FIG. 2, in which the measuring tube and a pressure transducer are replaced by a reservoir 20 placed on an electronic weigh scale 21. In this configuration the process is identical except that the signal from the weigh scale replaces the signal from the pressure transducer, and it is essential that the pipes that supply and extract liquid from the reservoir do not disturb the electronic balance. The overflow pipe may be removed and replaced by a dip contact 22 to ensure that the reservoir 20 is not overfilled.

What is claimed is:

1. A system for continuous delivery of a measured flow of liquid to a processing apparatus, the system comprising:
    a reservoir for holding a bulk supply of the liquid;
    an intermediate vessel;
    a first pump for supplying liquid from the intermediate vessel to processing equipment at a first rate;
    a second pump for supplying liquid from the reservoir to the intermediate vessel at a second rate, the second rate being faster than the first rate; and
    a controller comprising:
        a sensor adapted to determine when the weight of liquid in the intermediate vessel has reached a minimum position to initiate operation of the second pump to refill the vessel and adapted to terminate operation of the second pump when the weight of liquid in the intermediate vessel has reached a maximum position; and
        a monitor adapted to continuously monitor the weight of liquid in the intermediate vessel to determine a mass flow rate of liquid from the intermediate vessel and adapted to adjust the first pump while the liquid in the intermediate vessel falls from the maximum position to the minimum position such that the mass flow rate of liquid from the intermediate vessel substantially matches a required flow rate of the processing equipment.

2. A system as claimed in claim 1, wherein the sensor comprises a pressure transducer adjacent the intermediate vessel for determining the weight of any liquid therein.

3. A system as claimed in claim 1, wherein the controller for initiating operation of the second pump to recharge the intermediate vessel from the reservoir deactivates the control of the first pump in accordance with the mass flow rate of liquid from the intermediate vessel, and the first pump runs at a constant rate during the period of replenishment of the intermediate vessel.

4. A system as claimed in claim 1, further comprising a third pump configured to return any unused liquid in the intermediate vessel to the reservoir.

5. A system for continuous delivery of a measured flow of liquid to a processing apparatus comprising:
    a reservoir for holding a bulk supply of the liquid,
    an intermediate vessel,
    first means for pumping liquid from the intermediate vessel to processing equipment at one rate,
    second means for pumping liquid from the reservoir to the intermediate vessel at a second faster rate, and
    means for controlling a mass flow rate of liquid pumped from the intermediate vessel, the means for controlling comprising:

means for determining when the weight of liquid in the intermediate vessel has reached a minimum position to initiate operation of the second means for pumping to refill the vessel;

means for terminating operation of the second means for pumping when the liquid level in the vessel reaches a maximum position; and means for monitoring continuously the weight of liquid in the intermediate vessel and for determining the mass flow rate of liquid from the intermediate vessel and for adjusting the first means for pumping while the liquid in the intermediate vessel falls from the maximum position to the minimum position such that the mass flow rate of the liquid from the intermediate vessel substantially matches a required flow rate of the processing equipment.

6. The system in claim 5, wherein the intermediate vessel has a pressure transducer positioned adjacent the bottom of the intermediate vessel for determining the weight of any liquid therein.

7. A system as claimed in claim 5, wherein the means for controlling for initiating operation of the second means for pumping to recharge the intermediate vessel from the reservoir deactivates the control of the first means for pumping in accordance with the mass flow rate of liquid from the intermediate vessel, the first means for pumping running at a constant rate during the period of replenishment of the intermediate vessel.

8. A system as claimed in claim 5, wherein a further pump arrangement is provided to return any unused liquid in the intermediate vessel to the reservoir.

* * * * *

UNITED STATES PATENT AND TRADEMARK OFFICE
CERTIFICATE OF CORRECTION

PATENT NO. : 6,840,744 B2
DATED : January 11, 2005
INVENTOR(S) : David Watling

It is certified that error appears in the above-identified patent and that said Letters Patent is hereby corrected as shown below:

Title page,
Item [57], ABSTRACT,
Line 13, change "refill to vessel" to -- refill the vessel --

Column 1,
Line 35, before "gaseous sterilisation" insert -- a --
Line 59, after "liquid" change "form" to -- from --

Column 3,
Line 51, before "container using a dip tube." insert -- the --

Signed and Sealed this

Twelfth Day of July, 2005

JON W. DUDAS
*Director of the United States Patent and Trademark Office*